US006248939B1

(12) United States Patent
Leto et al.

(10) Patent No.: US 6,248,939 B1
(45) Date of Patent: Jun. 19, 2001

(54) CORN PLANTS AND PRODUCTS WITH IMPROVED OIL COMPOSITION

(75) Inventors: Kenneth Joseph Leto, West Des Moines, IA (US); James Francis Ulrich, Aurora, IL (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 08/693,079

(22) PCT Filed: Feb. 15, 1995

(86) PCT No.: PCT/US95/02076

§ 371 Date: Aug. 26, 1996

§ 102(e) Date: Aug. 26, 1996

(87) PCT Pub. No.: WO95/22598

PCT Pub. Date: Aug. 24, 1995

Related U.S. Application Data

(63) Continuation-in-part of application No. 08/196,622, filed on Feb. 15, 1994, now abandoned.

(51) Int. Cl.$^7$ ................................ A01H 5/00; A01H 4/00
(52) U.S. Cl. .................... 800/320.1; 800/298; 800/275
(58) Field of Search ................... 800/200, 205, 800/230, 235, 250, DIG. 56, 320.1, 298, 275; 47/58, DIG. 1; 435/172.3, 172.1, 424, 430, 430.1

(56) References Cited

U.S. PATENT DOCUMENTS

| 4,351,130 | 9/1982 | Rutger et al. | 47/58 |
|---|---|---|---|
| 4,545,146 | 10/1985 | Davis | 47/58 |
| 4,627,192 | 12/1986 | Fick | 47/58 |
| 4,658,084 | 4/1987 | Beversdorf et al. | 800/1 |
| 4,658,085 | 4/1987 | Beversdorf et al. | 800/1 |

FOREIGN PATENT DOCUMENTS

| 2220969 | 4/1974 | (FR) | A01H/1/02 |
|---|---|---|---|
| 92/01367 | 2/1992 | (WO) | A01H/1/02 |
| 92/08341 | 5/1992 | (WO) | A01H/1/02 |

OTHER PUBLICATIONS

*Corn Oil*, Corn Refiners Assoc., Inc., 1001 Connecticut Ave., NW, Washington, DC 20036, 1986, 24 pages.
Fitch, B., *JAOCS*, 62(11), 1985, 1524–1531.
Mensink, R.P. et al, *New England Journal of Medicine*, 323, 1990, 439–445.
Miller, M.F. et al, *J. Anim. Soc.*, 68, 1990, 1624–1631.
St. John, L.C. et al, *J. Anim Sci.*, 64, 1987, 1441–1447.
Mattson, F.R., et al, *J. Lipid Res.*, 26, 1985, 194.
Kiesselbach, T.A., *The Structure and Reproduction of Corn*, 1980, Univ. of Nebraska Press.
Rieger, R. et al, *A Glossary of Genetics and Cytogenetics*, 1968, Springer–Verlag, New York (unavailable).
Alexander, D.E. et al, *Relationship of Kernal Oil Content to Yield in Maize Crop Science*, 8, 1968, 272–274.
"Lipid Metabolism", In: *Introduction to Plant Biochemistry*, 2nd Ed., 1983, Pergamon Press, Goodwin and Mercer, Eds., pp. 273–274.
Poneleit, C.G. et al, *Science*, 147, 1965, 1585–1586.
de la Roche et al, *Crop Science*, 11, 1971, 856–859.
Jellum, M.D., *J. Hered.*, 57, 1966, 243–244.
Glover, D.V. et al, "Corn", In: *Nutritional Quality of Cereal Grains: Genetic & Agronomic Improvement*, Agronomy Monograph No. 28, Copyright 1987, ASA–CSSA–SSSA, 677 South Segoe Rd., Madison, WI 53711, USA, Chap. 7, pp. 183–336.
Jellum, M.D., *J. Agr.Food Chem.*, 18(3), 1970, 365–370.
Poneleit, C.G. et al, *Crop Science*, 10, 1970, 338–341.
Rooney, C.W. et al, 1987, Food Uses of Whole Corn and Dry–Milled Fractions, In: *Corn: Chemistry and Technology*, S.A. Watson and P.E. Ramstead, Eds., Amer. Assoc. of Cereal Chemists, Inc., St. Paul, MN pp. 399–429.
Eckhoff, S.R., Proceedings of the Fourth Corn Utilization Conference, Jun. 24–26, 1992, St. Louis, MO, printed by the National Corn Growers Association, CIBA–GEIGY Seed Division and the United States Dept. of Ag.
Weber et al., 1975, *Journal of the American Oil Chemist's Society*, 52(9), 370–373.
Miller et al., 1981, *Crop Science*, 21(3), 433–437.
Pamin et al., 1986, *Crop Science*, 26(2), 279–282.
Rao et al., 1990, *Indian Journal of Experimental Biology*, 28, 531–533.
Poehlman, J.M., "Breeding Field Crops", *AVI Publishing Co.*, Westport, (18) 469–476, 502 1986.
Wright, A., "A Gene Conditioning High Oleic Maize Oil, OLC1$^1$", *Maydica* (40) 85–88 1995.
CABA AN 80:87578 (Abstract).
CABA AN 95:198163 (Abstract).
James et al., "Isolation of EMS–induced Mutants in Arabidopsis Altered in Seed Fatty Acid Composition", *Theor. Appl. Genet.*, (80) 241–245 1990.
Weber E.J. et al., "Breeding for Lipid Composition in Corn", *Journal of the American Oil Chemist Society*, (52) 370–373 1975.
Jellum, M.D., "Plant Introductions of Maize as a Source of Oil with Unusual Fatty Acid Composition", *J. Agr. Food Chem.* (18)3 365–370 1970.
Database WPI, Derwent Publications, London, GB, AN 90–375699, Zeneca et al., Herbicide Resistance Maize Plants—obtd. by Mutagenesis of Pollen and Germination of Seed in Presence of Herbicide & JP 4, 507,340 (Imperial Chem Ind) See Abstract.
Mišević, D. et al., Twenty–Four Cycles of Phenotypic Recurrent Selection for Percent Oil in Maize. I. Per Se and Test–Cross Performance, *Crop Science*, 29, 320–324, 1989.

*Primary Examiner*—Gary Benzion

(57) ABSTRACT

This invention relates to corn (*Zea mays* L.) seed and grain having a significantly higher oleic acid content than conventional corn by virtue of heritable genes for increased oil and oleic acid content and/or lowered levels of linoleic acid. The present invention also relates to the production of high oil, high oleic grain, its oil, its progeny and its use.

16 Claims, No Drawings

CORN PLANTS AND PRODUCTS WITH IMPROVED OIL COMPOSITION

This application is a 371 of PCT/US95/02076 filed Feb. 15, 1995, which is a Continuation-in-part of Ser. No. 08/196,622 filed Feb. 15, 1994 now abandoned.

FIELD OF THE INVENTION

This invention relates to corn (*Zea mays* L.) seed and grain having a significantly higher oleic acid content by virtue of heritable genes for increased oil and oleic acid content and/or lowered levels of linoleic acid. The present invention also relates to the production of high oil, high oleic grain, plants and plant parts grown from such grain and uses of such improved grain.

TECHNICAL BACKGROUND OF THE INVENTION

Corn oil is comprised primarily of even-numbered carbon chain fatty acids. The distribution of fatty acids in typical corn oil is approximately 12% palmitic acid (16:0), 2% stearic acid (18:0), 25% oleic acid (18:1), 60% linoleic acid (18:2), and 1% linolenic acid (18:3). Palmitic and stearic acids are referred to as saturated fatty acids because their carbon chains contains only single bonds and the carbon chain is "saturated" with hydrogen atoms. Oleic, linoleic, and linolenic acids contain one, two, and three double bonds respectively, and are referred to as unsaturated fatty acids. Fatty acids in corn oil nearly always occur esterified to the hydroxyl groups of glycerol, thus forming triglycerides. Approximately 99% of refined corn oil is made up of triglycerides; Corn Oil, Corn Refiners Association, Inc., 1001 Connecticut Ave., NW., Washington, DC 20036, 1986, 24 pp.

When exposed to air, unsaturated fatty acids are subject to oxidation which causes the oil to have a rancid odor. Oxidation is accelerated by high temperatures, such as in frying conditions. The rate of oxidation is proportional to the number of double bonds in the fatty acids. Thus, linoleic acid with two double bonds is more unstable than oleic acid which has only one double bond. Oxidation reduces the shelf life of products containing corn oil because of the oil's high proportion of linoleic acid. Corn oil and products containing corn oil are often packaged under nitrogen in special packaging materials such as plastic or laminated foil, or are stored under refrigeration to extend their shelf life. These extra measures to reduce oxidation and subsequent rancidity add considerable cost to products containing corn oil.

Another measure to reduce the effects of oxidation on corn oil is to chemically hydrogenate the oil. This commercially important process by which hydrogen is added to double bonds of unsaturated fatty acids changes the physical properties of the oil and extends the shelf life of products containing corn oil. Hydrogenated vegetable oils are used to make margarine, salad dressings, cooking oils, and shortenings, for example. Approximately half a billion pounds, or roughly 40–50% of corn oil produced in the U.S. is used for cooking and for salad oils; Fitch, B., JAOCS, 1985, Vol. 62, no. 11, pp. 1524–31. Production of a more stable oil by genetic means would clearly have value by reducing or eliminating the time and input costs of chemical hydrogenation.

In addition to the economic factors associated with chemical hydrogenation of corn oil, there are human health factors that favor the production of a natural high oleic oil. During the hydrogenation process, double bonds in fatty acids are completely hydrogenated or are converted from the cis configuration to the trans configuration. Cis double bonds cause a fatty acid molecule to bend, which impairs crystallization and keeps the oil liquid at room temperature. During hydrogenation, cis bonds are straightened into the trans configuration, causing the oil to harden at room temperature. Recent studies on the effect of dietary trans fatty acids on cholesterol levels show that the trans isomer of oleic acid raises blood cholesterol level at least as much as saturated fatty acids, which have been know for some time to raise cholesterol in humans; Mensink, R. P. and B. K. Katan, N. Engl. J. Med., 1990, 323:439–45. Furthermore, the studies show that the undesirable low density lipoprotein level increases and the desirable high density lipoprotein level decreases in response to diets high in trans fatty acids. Large amounts of trans fatty acids are found in margarines, shortenings, and oils used for frying; the most abundant trans fatty acid in the human diet is the trans isomer of oleic acid, elaidic acid. A natural high oleic corn oil, which does not contain elaidic acid, will benefit consumers in general, and will particularly benefit those people who control their cholesterol level through their diet.

The human diet could also be improved by reducing saturated fat intake. Much of the saturated fat in the human diet comes from meat products. Poultry and swine diets often contain animal fat, which is high in saturated fatty acids, as an energy source. Non ruminant animals such as these are very susceptible to tissue fatty acid alteration through dietary modification; M. F. Miller, et al., J. Anim. Sci., 1990, 68:1624–31. A large portion of animal feed rations is made up of corn, which typically contains only about 4% oil. By replacing some or all of the supplemental animal fat in a feed ration with the oil present in high oil corn varieties, which contain up to 10% oil, it will be possible to produce meat products having less saturated fats. Feeding trials in which swine were fed diets high in oleic acid show that the amount of oleic acid deposited in adipose tissue can be raised substantially without adversely influencing the quality of the meat; M. F. Miller, et al., supra; L. C. St. John, et al., J. Anim. Sci., 1987, 64:1441–47. The degree of saturation of the fatty acids comprising an oil determines whether it is liquid or solid. In these studies, the animal diets high in oleic acid led to meat quality that was acceptable to the meat processing industry because of the low level of polyunsaturated fatty acids. Therefore, it can be extended that a feed ration containing high oleic, high oil corn would be preferable to one containing high oil corn which contains a high level of linoleic acid. Consumption of monounsaturated fatty acids decreases the LDL level without affecting the HDL level; Mattson, F. R., and S. M. Grundy, J. Lipid Res., 1985, 26:194. The HDL portion is responsible for removal of cholesterol from the body; L. C. St. John, supra. Processed meats produced from animals fed diets containing high oil, high oleic corn will be more healthful in the human diet.

The corn kernel is a product of double fertilization; Kiesselbach, T. A., 1980, The Structure and Reproduction of Corn, University of Nebraska Press. This means that both the diploid embryo (giving rise to the germ and seedling) and the triploid endosperm (the nutritive structure surrounding the germ) contain genes transmitted from both the male and female parents. Nonetheless, the genes affecting grain composition and quality are similar enough in most field corn inbreds that crossing any given female with a large variety of male plants does not result in dramatic changes in the compositional or quality characteristics of the resulting seed or grain. Likewise, planting different field corn hybrids within pollinating proximity to each other will not, in most cases, substantially affect the quality of the grain harvested on each type.

In contrast, a minority of commercial corn inbreds or hybrids do contain genes which substantially modify grain quality. These hybrids, include those containing the waxy gene. Such waxy gene hybrids must be isolated from normal, non-waxy corn inbreds or hybrids in order to recover waxy seed or grain. If a non-waxy pollen grain (as found in most field corn inbreds and hybrids) pollinates an ovule borne on a waxy inbred or hybrid, the resulting kernel will be non-waxy, even though adjacent kernels on the same ear, pollinated by waxy pollen, will remain waxy. This immediate effect of pollen genotype on kernel characteristics is termed "xenia", and the hybrid nature of such kernels is recognizable by particular phenotypic characteristics (color, shape, size, etc.) owing to the direct influence exerted by the genotype of the pollen; Rieger, R., A. Michaelis and M. M. Green, 1968, A Glossary of Genetics and Cytogenetics, Springer-Verlag, New York. This immediate effect of pollen genotype on grain quality has been observed with pollen obtained from high-oil corn plants; Alexander, D. E. and R. J. Lambert, 1968, Relationship of Kernel Oil Content to Yield in Maize Crop Science 8:272–274.

Production of oleic acid in corn is under genetic control, although the mode of inheritance is only partially understood. Oil production in the kernel occurs primarily in the germ. Fatty acid biosynthesis is regulated by a multi-step biochemical pathway whereby the saturated fatty acids, palmitic and stearic, are synthesized and subsequently dehydrogenated to oleic, linoleic, and linolenic acids; Lipid Metabolism, In: Introduction to Plant Biochemistry, 2nd Ed., 1983, Pergamon Press, Goodwin and Mercer, Eds., pp 273–327. A single gene locus, designated ln, was reported to be responsible for regulating the levels of oleic and linoleic acids in corn; Poneleit, C. G., and D. E. Alexander, Science, 1965, 147:1585–86. Subsequent studies show that the mode of inheritance of oleic acid is more complicated than first thought. At least two loci have been shown to regulate the oleic acid level; de la Roche et al., Crop Sci., 1971, 11:856–59. In a study involving eight different reciprocal crosses and their parental inbred lines, it was concluded that inheritance of increased oleic content in corn can result from dominant, partially dominant, and even recessive gene action; Jellum, M. D., J. Hered., 1966, 57:243–44. Only one report has been found in which the inheritance of oleic acid in a high oil corn line, IHO, is discussed; de la Roche, et al., supra. The report states that the quality of corn oil increases as the linoleic acid content increases. The data are presented in terms of the linoleic acid content, which for IHO is reported to be approximately 47% of the oil fraction. From our studies of thousands of samples, there is an inverse relationship between oleic acid and linoleic acid content. A line that is 47% linoleic acid would contain 35–40% oleic acid, which is substantially less than the oleic content in the present invention. Also, IHO is not an agronomically acceptable line and would not be used in commercial production; Glover, D. V., and E. T. Mertz, Corn, In Nutritional Quality of Cereal Grains: Genetic and Agronomic Improvement, Agronomy Monograph no. 28, Copyright 1987, ASA-CSSA-SSSA, 677 South Segoe Road, Madison, Wis. 53711, USA, Chapter 7, pp. 183–336; Fitch, B., JAOCS, 1985, Vol. 62, no. 11, pp. 1524–31.

A survey of plant introductions for fatty acid profile shows that greater genetic diversity exists in corn of foreign origin than exists in U.S. corn; Jellum, M. D., 1970, J. Agr. Food Chem., 18:3, pp. 365–70. Oleic acid content ranged from 14 to 64% in the plant introductions screened, which represented germplasm from over 50 foreign countries. Plant introductions are a valuable source of genetic diversity for many traits, including oleic acid content. However, breeding genes from plant introductions of foreign origin into elite U.S. adapted inbred lines is a costly process requiring three to six years.

A breeding strategy know as recurrent selection has been suggested as a means of increasing the oleic acid level in corn; Poneleit, C. G., and L. F. Bauman, Crop Sci., 1970, 10:338–41. This breeding method was applied to maize plant introductions and is the basis for a patent application for high oleic corn products and methods for their production; PCT/US91/04626. To have commercial utility, the value of a trait, such as high oleic oil, must be worth more than the costs associated with production, storage, and shipment of the grain. A bushel of shelled corn, which weighs approximately 56 pounds, can yield approximately two pounds of oil when milled. Because of the small amount of oil normally found in corn, the added value of an improved oil, such as high oleic oil, is unlikely to be sufficient to pay for the production and identity preservation costs, unless substantially greater oil is produced as in newly developed high oil corn varieties.

To have utility in an animal feed ration as a means of improving carcass quality and subsequently improving the human diet, high oleic corn must be capable of supplying enough oleic acid in the diet to raise the oleic acid level in the meat. Corn is included in animal feed as the main source of energy, the majority of which comes from the high starch content of corn, and other sources of energy such as animal fat, vegetable fat, or animal-vegetable fat blends are commonly added to increase the energy density of feed rations. For example, the amount of corn oil included in the corn fraction of a typical commercial poultry feed ration is about 2.5% in a ration that contains 65–70% corn. To increase the energy density of feed rations, highly saturated animal fat or animal-vegetable fat blends are added at approximately 5 to 8% of the diet. High oil corn with an energy content which is significantly higher than that of normal corn can reduce or totally eliminate the use of or need for added fat when used in a typical poultry ration.

A typical chicken broiler corn-soybean meal diet supplemented with an animal-vegetable fat blend contains approximately 1.937% oleic acid. Increasing the oleic acid content of the oil contained in corn used in a feed ration from the 25% found in normal corn to 60% (also in a normal or low oil variety) increases the oleic acid in the feed ration to 2.733%. Increasing the oleic acid content from 25% to 60% of the oil present in high oil corn grain that contains 8–10% oil increases the oleic acid content of the feed ration to 4.266%. These increases represent a 30% increase in oleic acid content when normal corn is used in the feed ration, and a 120% increase when high oil corn varieties are used. High oil corn can reduce or totally eliminate the need for added fat when used in a typical poultry ration, suggesting that modifications to the fatty acid profile of corn oil need to be made in a high oil corn variety to have utility in improving carcass quality. The high oleic corn lines described in the aforementioned patent application are not high oil corn lines.

Most cereal crops are handled as commodities, and many of the industrial and animal feed requirements for these crops can be met by common varieties which are widely grown and produced in volume. However, there exists at present a growing market for crops with special end-use properties which are not met by grain of standard composition. Most commonly, specialty maize is differentiated from "normal" maize, also known as field corn, by altered endosperm properties, such as an overall change in the degree of starch branching, as in waxy or high amylose maize, an increased accumulation of sugars as in sweet corn, or an alteration in the degree of endosperm hardness as in food grade maize or popcorn; Glover, D. V. and E. T. Mertz, 1987, Corn. In: Nutritional Quality of Cereal Grains; Genetic and Agronomic Improvement, R. A. Olson and K. J. Frey, eds. American Society of Agronomy, Madison, Wis., pp. 183–336; Rooney, L. W. and S. O. Serna-Saldivar, 1987, Food Uses of Whole Corn and Dry-Milled Fractions, In: Corn:Chemistry and Technology, S. A. Watson and P. E. Ramstead, eds. American Association of Cereal Chemists, Inc., St. Paul, Minn., pp. 399–429. "Specialty" crops are typically grown under contract for specific end users who place value on starch quality or other specific quality attributes. A specialty crop such as waxy maize is more valuable as a raw material to the starch industry than is normal or commodity grade maize, and thus is referred to as a value added crop. Currently the market size and added value of waxy maize is such that approximately 150,000 acres are grown in the United States. Farmers are paid a premium for growing specialty crops such as waxy maize because it is more valuable than normal maize and must not be mixed with normal maize. Because of the desire of many humans to eat a healthier diet and the documented effects of oleic acid on reducing cholesterol, the present invention will have greater value than normal corn. The current invention offers farmers the opportunity to grow a higher value crop than normal maize.

Oil is obtained from plants by a milling process. Corn oil is extracted from kernels through the use of a either a wet or dry milling process. Wet milling is a multi-step process involving steeping and grinding of the kernels and separation of the starch, protein, oil, and fiber fractions. A review of the maize wet milling process is given by S. R. Eckhoff in the Proceedings of the Fourth Corn Utilization Conference, Jun. 24–26, 1992, St. Louis, Mo., printed by the National Corn Growers Association, CIBA-GEIGY Seed Division and the United States Department of Agriculture. Dry milling is a process by which the germ and hull of the corn kernel are separated from the endosperm by the controlled addition of water to the grain and subsequent passage through a degerming mill and a series of rollers and sieves. The U.S. dry milling industry produces approximately 50 million pounds of crude corn oil per year, and the wet milling industry produces over one billion pounds of crude corn oil; Fitch, 1985, supra. The present invention offers the wet and dry milling industries the opportunity to process and sell a higher value oil than normal corn oil.

SUMMARY OF THE INVENTION

Applicants have discovered a corn plant capable of producing grain having a ten fold increase in oleic acid content over normal corn by breeding a high oil corn variety with a corn variety that carries a chemically mutated gene that confers high oleic acid content. Specifically, a corn plant has been bred to produce grain having 17 to 20% oil, with about 60% of the oil being oleic acid. Plants of this type can be used to pollinate high yielding, commercially acceptable hybrids that are male sterile, which have high oleic acid producing characteristics, thus producing grain having a five fold increase in oleic acid content over normal corn. By using this method and pollinator plants of this type, the timeline for commercial production of corn having elevated oleic levels is greatly accelerated.

This invention consists of corn grain produced by planting in close proximity, preferably in a field, corn plants of an agronomically elite high-yielding female parent, having high oleic characteristics, and optionally having high-oil characteristics, with corn plants of a high-oil and high oleic male parent, optionally having high-yielding characteristics and/or agronomically elite characteristics. The grain may then be all harvested or harvested selectively, for example, so that kernels produced by the female plants are harvested as grain. In the planting described, the preferred high-oil, high oleic male parent plant, when self or sib pollinated, is capable of producing kernels having a total oil content ranging from 7.5% to 20% of the total seed weight, measured at zero percent moisture and an oleic acid content of not less than about 55% of the total oil content of the seed. The agronomically elite female parent, when self or sib pollinated, is capable of producing kernels having a total oil content of between about 2 percent to about 7.5 percent, preferably at least about 6%, of the total seed weight, measured at zero percent moisture, wherein the oleic acid content is not less than about 55% of the total oil content.

The grain produced has as oleic acid content of about 4% to about 7% of the total seed weight.

The present invention further comprises a corn oil, produced from the grain described above, which has 50% to 120% greater oxidative stability than that of "normal" corn oil where the oxidative stability is obtained without the addition of antioxidants. Such oil is useful in human and animal food, in cooking, and in industrial applications.

Also taught herein is a method of developing corn varieties with altered levels of fatty acid compositions, including oleic acid, comprising treatment of seeds or pollen with a chemical mutagen to produce mutant plants. Mutagens useful herein are selected from ethylmethanesulfonate and nitrosomethylurea. Also taught is a corn variety produced by such method having total oleic acid content of not less than about 55% of the total oil content of the seed, when measured at about zero percent moisture.

A further embodiment of the invention relates to the use of high oil, high oleic grain as an animal feed to improve meat quality, particularly in swine and poultry.

The present invention further comprises mutant corn lines B73OL and AEC272OL lines which bear the ATCC accession numbers 97026, 97027, from which the high oleic characteristics of the male and female plants that are crossed, as described above, are generated. The invention also describes the high oil, high oleic corn variety resulting from the cross, ASKC28 X B73OL, which bears the ATCC accession number 97042. The mutant corn lines deposited under ATCC accession numbers 97026 and 97207 were deposited under terms conforming to the Budapest Treaty on Jan. 27, 1995.

DETAILED DESCRIPTION OF THE INVENTION

The present invention provides corn plants that produce grain having a mean oleic acid content of about ten percent, or approximately ten times the oleic acid content of "normal" corn. A valuable property of this higher oleic acid type of corn is the increased oxidative stability of its oil. Use of the grain, produced by these corn plants, in feeding results in improved carcass quality of animals.

One method of enhancing the oleic acid content of corn grain comprises a planting, as described in the Summary of the Invention, involving the steps of:

(a) planting in close proximity, in a field:
  (1) corn seed of a high-yielding, agronomically elite variety to obtain female (i.e., male sterile) corn plants which have a high oleic acid characteristics, and which may or may not have an oil content greater than that of normal corn; and (2) corn seed of high-oil, high oleic variety male corn plant, which may or may not have high yielding characteristics, and which further may or may not be nonisogenic to said female corn plants, so as to produce high-oil, high oleic corn plants capable of serving as pollinators, (b) permitting said high-oil, high oleic corn plants to pollinate said female corn plants;

(c) harvesting the resulting corn grain on said corn plants, thereby obtaining a high yield of corn grain possessing an oil concentration not less than about 7.5% and oleic acid content intermediate between that found in kernels obtained following self-pollination of said pollinator and said female corn plants.

To facilitate cross pollination, the plants to be used as the female are rendered male sterile. This can be accomplished by physical removal of the male pollen-shedding part of the plant, by chemical treatment, or by a genetic mechanism such as cytoplasmic male sterility. In maize, the male part of the plant is the tassel which can be easily removed by hand or machine. Production of the present invention in maize requires planting male and female genotypes in adjacent rows in the field or, preferably, intermixed within the same rows. Female plants are rendered male sterile, preferably through genetic means, and are pollinated by male plants. Grain is harvested from female and male plants for subsequent oil extraction.

It has also been observed that a gene altered through chemical mutagenesis can be used to alter the oleic acid level as it confers the same increase in oleic acid as a percent of total oil in corn seeds that contain about 20% oil as in seeds that contain only about 4% oil.

A major advantage of oil obtained from grain produced in accordance with the present invention is that it possesses greater oxidative stability than normal corn oil, without employing antioxidants. When used in food and frying applications, oil obtained from the grain of the present invention will have a longer shelf life or fry life and will not develop rancid odors as quickly as normal corn oil. Oil of the present invention can replace chemically hydrogenated oil in applications where oxidative stability is desired.

For purposes of this application, unless otherwise noted, the oleic acid content or % oleic acid is the percent of the total fatty acids in the oil, which also includes, but is not limited to, palmitic acid, stearic acid, linoleic acid, and linolenic acid.

In the context of this disclosure, a number of terms shall be utilized relevant to plant breeding and oil characterization. As used herein, an "allele" is one of two or more forms of a gene that exists at a chromosome location. The term "corn" refers to any variety, cultivar or population of Zea mays L. The terms "commercially acceptable" or "elite" characterize a plant or variety possessing favorable traits, such as, but not limited to, high yield, good grain quality, and disease resistance. This enables its use in commercial production of seed or grain at a profit. These terms also characterize parents giving rise to such plants or varieties. "Field corn" refers to varieties or cultivars of corn grown extensively in large acreage for the production of grain and/or forage. Most field corn in the United States is also referred to as dent corn, whereas field corn produced in Europe and Argentina is more likely to be referred to as flint corn. The "germ" is the embryo of the corn kernel and contains the vast majority of the oil found in the kernel. "Grain" comprises mature corn kernels produced by commercial growers for on farm use or for sale to customers in both cases for purposes other than growing or reproducing the species. Typical customers would include livestock feeders, wet or dry millers, or animal feed formulators.

The term "heterozygous" describes a genetic condition existing when different alleles reside at corresponding loci on homologous chromosomes. A "high-oil corn kernel" is one which contains elevated levels of oil on a percent dry weight basis when compared to low-oil corn kernels. A "high-oil corn plant" is a plant which, when self pollinated, will give rise to kernels containing elevated levels of oil on a percent dry weight basis when compared to a low-oil corn plant. The term "homozygous" describes a genetic condition existing when identical alleles reside at corresponding loci on homologous chromosomes. A "hybrid" represents any offspring of a cross between two genetically unlike individuals; Rieger R., A. Michaelis and M. M. Green, 1968, A Glossary of Genetics and Cytogenetics, Springer-Verlag, New York. An "inbred" is a substantially homozygous plant or variety. The "kernel" is the corn caryopsis, consisting of a mature embryo and endosperm which are products of double fertilization. A "low-oil corn kernel" contains oil in the range of about 2.5 to 5.1 percent on a dry weight basis. A "low-oil corn plant" is one which, when self pollinated, will give rise to kernels containing levels of oil in the range of 2.5 to 5.1 percent on a dry weight basis. This level of oil is typical of a wide range of field corn inbreds and hybrids. The term "maize" represents any variety, cultivar, or population of Zea mays L. "Male sterile" refers to plants which fail to produce functional pollen as a consequence of mechanical or hand detasseling, incorporation of genetic sterility, or by other mechanisms.

As used herein "nonisogenic" is a state of genetic dissimilarity between individual inbreds, hybrids or varieties.

As used herein, "normal corn" describes corn grain in which the oleic acid content of the oil ranges from 20–30% of the total fatty acids and the oil content is 2.5 to 5.1 percent on a dry weight basis.

As used herein in describing "oleic acid content", the term "high oleic" refers to a grain or seed having an oleic acid content of not less than about 50% of the total oil content of the seed, by weight measured at 0% moisture.

The "ovule" portion of the plant is a structure consisting of female reproductive tissue surrounded by maternal tissue. During the development of a corn plant the ovule will eventually house a haploid egg nucleus and two haploid polar nuclei. Following fusion with sperm nuclei found in pollen, the ovule will develop into a mature corn kernel. The "percent (%) oil" is the oil concentration of a corn kernel expressed on a dry weight basis. A "plant introduction" represents a collection of seeds or plants of the same species and region of origin which have been transported from one region to another. A large plant introduction collection is maintained by the United States Department of Agriculture. Plant introductions can be used by breeders as a source of genetic variation, but are not elite and often require extensive breeding to move desirable genes from the plant introduction into adapted varieties. The "pollen" is a structure which ultimately contains the two haploid sperm nuclei which fuse with the egg nucleus and polar nuclei found in the ovule to give rise to the embryo and endosperm of the mature corn kernel. A "population" is a genetically heterogeneous collection of plants sharing a common genetic derivation. The "seed" is the mature corn kernel produced for the purpose of propagating the species and for sale to commercial growers. A "synthetic" or "synthetic population" is a genetically heterogeneous collection of plants of known ancestry created by the intermating of any combination of inbreds, hybrids, varieties, populations, races, or other synthetics. The terms "variety" or "cultivar" refer to a group of similar plants that by structural features and performance can be identified from other varieties within the same species.

Kernels from the plants of the present invention express a greater amount of oil and an improved oil composition relative to commercial varieties. The improvements relate to oxidative stability of the oil and to human health when the oil is used in food products, including its use as a cooking oil. The fatty acid profile of oil extracted from these varieties is dramatically different from the profiles seen in currently grown elite corn varieties.

Applicants teach a method for producing the novel corn varieties of the present invention and teach a method for producing high yielding elite varieties having substantial increases in oleic acid content.

EXAMPLES

The present invention is further defined in the following Examples. It will be understood that these Examples, while indicating preferred embodiments of the invention, are given by way of illustration only. The present invention can be used for any purpose where its properties are useful such as in, but not limited to, foods, frying oils, animal feeds, pharmaceuticals, and industrial oils. In the below Examples, where oil percents are expressed as percents of seed weight, zero percent moisture is presumed. Oleic acid content in Tables 1–5 is expressed as a percent of the total oil content of the seed. The calculation of oleic acid content as a percent of seed weight is carried out by multiplying the percent oil by the percent oleic acid.

Example 1
Breeding Methodology for Production of High Oil, High Oleic Germplasm

This example illustrates the creation of maize germplasm having a ten fold increase in oleic acid content over normal maize. Maize plants capable of producing oil having nearly three times the oleic acid content of normal maize were produced using a pollen mutagenesis technique described by M. G. Neuffer and E. H. Coe Jr., Maydica, 1978, 23:21–28. Two genotypes were mutagenized, and high oleic mutants were recovered in both. Maize plants of the background B73, an inbred line developed at Iowa State University and available to the public, and AEC272, a high oil line developed by the University of Illinois and licensed for commercial use exclusively by E. I. du Pont de Nemours and Company and Pfister Hybrid Corn Company were mutagenized. Pollen was collected from field-grown plants and sifted to remove anthers. Pollen was suspended and stirred constantly for 30 minutes in a solution of paraffin oil and ethyl methane sulfonate (EMS). Three concentrations of EMS were used for B73OL, 0.053%, 0.0625%, and 0.083%. One concentration, 0.0625%, was used for AEC272OL. The treated pollen was then brushed onto silks using a small paint brush.

Seeds (kernels) that developed on ears pollinated with treated pollen were subsequently germinated and plants were self pollinated. The seeds resulting from these plants were planted an additional time and self pollinated. Kernels were collected from individual self pollinated ears of B73 and analyzed using a Tecator™ Infratech Model 1255 near infrared transmission (NIT) spectrophotometer calibrated to detect kernels with elevated oleic content (Tecator AB, Box 70, S-263 21, Hoganas Sweden; Williams, P. C., 1987, Commercial Near Infrared Reflectance Instrumentation, In: Near Infrared Technology in the Agricultural and Food Industries; Williams, P. C. and C. Norris, eds. American Association of Cereal Chemists). A sample of kernels from those ears that were identified as bearing high oleic kernels by NIT were subjected to gas chromatography to further quantify their oleic acid content. Kernels from one ear averaging two to three times the oleic acid content of normal corn following gas chromatography were given the inbred line designation B73OL. The inbred family ACE27-2OL was similarly identified by analysis of kernels from original self pollinated ears of ACE272, although the NIT screen was omitted.

To accurately determine the oleic acid content, oil was extracted from 30 mg of ground corn using the following protocol:

1. Finely ground corn was placed in a 13×100 mm screw top tube.
2. 0.25 ml of a working solution of sodium methoxide was added. The working solution contains 20 ml of a 25% sodium methoxide added to 200 ml of methanol.
3. 1.0 ml of hexane was added.
4. The sample was mixed on a rotary shaker for 30 minutes.
5. 0.1 ml of 10% acetic acid was added.
6. The sample was vortexed, then centrifuged for 5 minutes at 2500 RPM.
7. Hexane was removed and the sample was placed in a gas chromatograph vial.
8. Fatty acid composition of the samples was determined using a Hewlett-Packard Model 5890 gas chromatograph.

At least 20 bulked kernels per F3 ear were used to determine oil and fatty acid composition. Oil produced by certain plants developed using this mutagenesis protocol contains approximately 60% oleic acid, or two to three times oleic acid produced in the non-mutant versions of these two genotypes.

Genetics studies with the high oleic B73 mutant showed that elevated oleic content in this line is conferred by a single gene which displays additive inheritance. Plants carrying the mutant gene were cross pollinated with plants of the background ASKC28, a high oil variety developed by the University of Illinois and licensed for commercial use exclusively by E. I. du Pont de Nemours and Company and Pfister Hybrid Corn Company. ASKC28 is a population of corn plants ranging in oil content from 7–22% and averages 18% oil. Average oleic acid content as a percentage of the oil in ASKC28 ears is 43%, and no ears in this population have been found to be above 50% oleic acid. F1 plants of this cross were self pollinated and F2 seeds were planted and the resulting plants were self pollinated to give a population of 956 F3 ears. Seed oil content was determined for F3 ears using a Tecator™ Infratech Model 1255 near infrared spectrophotometer calibrated against standard gravimetric oil determinations (Tecator AB, Box 70 S-263 21, Hoganas Sweden; Williams, P. C., 1987, Commercial Near Infrared Reflectance Instrumentation, In: Near Infrared Technology in the Agricultural and Food Industries; Williams, P. C. and C. Norris, eds. American Association of Cereal Chemists). For calibration purposes, the total oil concentration of shelled kernels was determined gravimetrically according to Method 920.39 of the Association of Official Analytical Chemists. Oleic acid content was determined by gas chromatography.

Of the 956 F3 ears, 49 had oil contents in the 15–20% range. Of these 49 ears, 3 had oleic contents above 60%, and 3 had oleic contents from 55–60% (Table 1). These oleic levels are higher than any that have been seen in the ASKC28 population, and are in the range of those seen in the B73 EMS derived mutant. Ear number 1125.04 had an oil content of 17.3% and an oleic acid content of 59.5%, which represents approximately a 10 fold increase in the total oleic acid as a percentage of the seed compared to normal corn.

Plants were grown from selection 1125.04 and were cross pollinated with another F3 selection of the same pedigree having an oil content of 15% and and oleic acid content of 59%. Plants arising from this cross were self pollinated and ears were analyzed for oil and oleic acid content. By crossing these two high oil, high oleic lines together, it was possible to create kernels having about 20% oil and about 60% oleic acid (Table 2).

These findings show that the mutant gene that confers the high oleic trait in the low oil corn line B73 is also effective in reducing the conversion of oleic acid to linoleic acid in seeds that produce over 5 times more oil. These results were unexpected assuming that the mutant gene confers a partial block in the oil biosynthetic pathway from oleic to linoleic acid. Until the discovery of the present invention, it was not known whether the total oleic acid as a percent of the seed would be greater than the total oleic acid percent of the B73 mutant which is low in oil. Organisms can find ways to circumvent blocks in biochemical pathways by using other enzymatic pathways. It was not known that the distribution of fatty acids, with particular reference to oleic acid, could be essentially the same for a seed that produces 17 to 20% oil as it is for a seed that produces only 4% oil.

TABLE 1

Oil and Oleic Acid Content of the 49 Highest Oil F3 Ears from a Population of 956 F2 Plants of the Cross ASKC28 × B73OL

|  | EAR ID NO. | % OLEIC | % OIL |
|---|---|---|---|
| 1 | 1008.04 | 64.1 | 15.4 |
| 2 | 1048.01 | 60.7 | 15.0 |
| 3 | 1022.05 | 60.5 | 15.6 |
| 4 | 1125.04 | 59.5 | 17.3 |
| 5 | 1056.05 | 57.5 | 15.0 |
| 6 | 1015.06 | 56.1 | 15.7 |
| 7 | 1131.11 | 51.0 | 15.0 |
| 8 | 1041.01 | 47.6 | 17.4 |
| 9 | 1009.04 | 47.4 | 16.7 |
| 10 | 1058.03 | 47.2 | 15.7 |
| 11 | 1117.07 | 46.9 | 16.2 |
| 12 | 1084.06 | 46.5 | 20.0 |
| 13 | 1024.01 | 46.4 | 17.7 |
| 14 | 1089.04 | 46.0 | 16.2 |
| 15 | 1108.04 | 45.1 | 17.5 |
| 16 | 1096.02 | 44.3 | 15.7 |
| 17 | 1031.03 | 43.7 | 17.3 |
| 18 | 1031.01 | 43.3 | 20.0 |
| 19 | 1047.11 | 43.2 | 17.6 |
| 20 | 1063.07 | 42.8 | 15.4 |
| 21 | 1047.04 | 42.6 | 16.2 |
| 22 | 1118.07 | 42.6 | 15.8 |
| 23 | 1030.07 | 42.5 | 16.1 |
| 24 | 1100.03 | 42.2 | 18.4 |
| 25 | 1059.02 | 41.9 | 16.0 |
| 26 | 1072.02 | 41.5 | 15.5 |
| 27 | 1028.07 | 39.7 | 17.2 |
| 28 | 1028.07 | 39.7 | 16.6 |
| 29 | 1066.01 | 39.6 | 16.6 |
| 30 | 1096.05 | 39.4 | 17.3 |
| 31 | 1103.06 | 39.4 | 16.0 |
| 32 | 1014.05 | 38.4 | 16.0 |
| 33 | 1045.09 | 38.1 | 15.4 |
| 34 | 1006.10 | 38.1 | 15.1 |
| 35 | 1098.07 | 37.9 | 20.3 |
| 36 | 1118.04 | 37.6 | 17.4 |
| 37 | 1043.06 | 37.4 | 17.2 |
| 38 | 1020.01 | 37.0 | 18.4 |
| 39 | 1048.06 | 37.0 | 16.1 |
| 40 | 1101.01 | 36.7 | 20.3 |
| 41 | 1066.09 | 36.6 | 16.2 |
| 42 | 1101.03 | 36.4 | 19.2 |
| 43 | 1101.02 | 35.7 | 20.7 |
| 44 | 1101.04 | 35.2 | 22.4 |
| 45 | 1090.01 | 34.5 | 15.0 |
| 46 | 1109.01 | 33.6 | 15.3 |
| 47 | 1083.03 | 32.8 | 15.2 |
| 48 | 1111.02 | 30.4 | 17.1 |
| 49 | 1030.04 | 29.0 | 15.4 |

TABLE 2

Oil and Oleic Acid Content of S1 Ears Derived from a Cross Between Two S3 ASKC28 × B73OL Lines Having 15–17% Oil and 60% Oleic Acid

|  | EAR ID NO. | % OIL | % OLEIC |
|---|---|---|---|
| 1347 | BAR06360 | 14.99 | 58.6 |
| 1347 | BAR06361 | 14.48 | 61.0 |
| 1347 | BAR06362 | 13.80 | 60.9 |
| 1347 | BAR06363 | 18.08 | 60.6 |
| 1347 | BAR06364 | 12.25 | 58.8 |
| 1348 | BAR06376 | 17.36 | 60.5 |
| 1348 | BAR06377 | 17.57 | 58.2 |
| 1348 | BAR06378 | 10.57 | 63.7 |
| 1348 | BAR06379 | 10.64 | 59.5 |
| 1348 | BAR06380 | 13.16 | 60.9 |
| 1348 | BAR06381 | 15.96 | 58.9 |
| 1348 | BAR06382 | 11.65 | 63.2 |
| 1348 | BAR06383 | 15.90 | 60.4 |
| 1348 | BAR06384 | 16.81 | 59.2 |
| 1348 | BAR06385 | 13.95 | 62.1 |
| 1348 | BAR06386 | 11.59 | 61.0 |
| 1348 | BAR06387 | 16.37 | 58.8 |
| 1348 | BAR06388 | 10.65 | 56.3 |
| 1348 | BAR06389 | 13.60 | 54.8 |
| 1348 | BAR06390 | 16.53 | 56.2 |
| 1349 | BAR06401 | 16.76 | 60.6 |
| 1349 | BAR06402 | 17.28 | 57.2 |
| 1349 | BAR06403 | 12.58 | 52.4 |
| 1349 | BAR06404 | 16.55 | 62.2 |
| 1349 | BAR06405 | 17.07 | 60.7 |
| 1349 | BAR06406 | 15.53 | 55.1 |
| 1349 | BAR06407 | 15.19 | 58.9 |
| 1349 | BAR06408 | 15.61 | 63.3 |
| 1349 | BAR06409 | 14.99 | 58.0 |
| 1349 | BAR06410 | 19.49 | 61.1 |
| 1349 | BAR06411 | 17.19 | 61.6 |
| 1349 | BAR06412 | 17.99 | 60.4 |
| 1349 | BAR06413 | 13.80 | 53.4 |
| 1349 | BAR06414 | 18.39 | 62.3 |
| 1349 | BAR06415 | 17.03 | 61.2 |
| 1350 | BAR06427 | 19.09 | 61.4 |
| 1350 | BAR06428 | 19.14 | 64.1 |
| 1350 | BAR06429 | 17.01 | 57.5 |
| 1350 | BAR06430 | 17.62 | 64.5 |
| 1350 | BAR06431 | 17.53 | 63.7 |
| 1350 | BAR06432 | 20.21 | 58.1 |
| 1350 | BAR06434 | 17.72 | 59.2 |
| 1350 | BAR06435 | 18.02 | 60.9 |
| 1350 | BAR06436 | 19.29 | 62.7 |
| 1350 | BAR06437 | 16.90 | 61.2 |

TABLE 2-continued

Oil and Oleic Acid Content of S1 Ears Derived from a Cross Between Two S3 ASKC28 × B73OL Lines Having 15–17% Oil and 60% Oleic Acid

| | EAR ID NO. | % OIL | % OLEIC |
|---|---|---|---|
| 1350 | BAR06438 | 18.54 | 60.0 |
| 1350 | BAR06439 | 19.75 | 61.9 |
| 1350 | BAR06440 | 14.38 | 62.9 |
| 1351 | BAR06451 | 14.75 | 53.8 |
| 1351 | BAR06452 | 13.00 | 59.4 |
| 1351 | BAR06453 | 12.43 | 57.4 |
| 1351 | BAR06454 | 14.97 | 58.1 |
| 1351 | BAR06455 | 17.47 | 58.4 |
| 1351 | BAR06456 | 11.27 | 62.5 |
| 1351 | BAR06457 | 12.17 | 56.2 |
| 1351 | BAR06458 | 12.45 | 60.5 |
| 1351 | BAR06459 | 13.84 | 59.1 |
| 1351 | BAR06460 | 16.58 | 56.6 |
| 1351 | BAR06461 | 18.38 | 60.0 |
| 1351 | BAR06462 | 15.28 | 60.6 |
| 1352 | BAR06476 | 11.43 | 61.5 |

Example 2

Production of High Oil, High Oleic Acid Corn Grain

This example illustrates the production of agronomically elite, high yielding corn plants which bear grain having approximately a five fold increase in oleic acid content over normal corn. Maize plants of the genotype B73OL were pollinated by plants of the genotype AEC272OL to produce F1 seed. F1 hybrid plants of this cross were either self pollinated or cross pollinated by F3 plants obtained from samples 1008.04, 1022.05, 1048.01, and 1125.04 listed in Table 1. Self pollinated ears derived from samples 1008.04, 1022.05, 1048.01, and 1125.04 varied for oil and oleic acid content from ear to ear, which is not unexpected for F3 generation plants. One F3 derived ear was 17.1% oil and 67% oleic acid, indicating that the present discovery is repeatable under very different environmental conditions. The initial discovery of samples 1008.04, 1022.05, 1048.01, and 1125.04 was made in plants grown during the summer in Newark, Del. The following generation which gave rise to plants with 15 to 17% oil and 60 to 65% oleic acid was grown in the winter in Molokai, Hi. Self pollinated F1 plants of the cross B73OL X AEC272OL produce grain having an oil content of approximately 6% and an oleic acid content of the oil of approximately 60%. When cross pollinated by F3 plants derived from samples 1008.04, 1022.05, 1048.01, and 1125.04, grain produced on female F1 B73OL X AEC272OL plants averages 8.4% oil and 62.8% oleic acid. Oil and oleic acid levels of individual ears comprising this grain are shown in Table 3. Oil and oleic acid content are similar for grain produce in this manner under different environmental conditions. Data presented in Table 3 represent grain produced in the winter in Molokai, Hi., and bulked grain produced in the same manner in the summer near Newark, Del. averaged 9.6% oil and 64.1% oleic acid.

TABLE 3

Oil and Oleic Acid Content of Grain Resulting from the Cross Pollination of B730L × AEC2720L Ears by Pollen From F3 Derived Plants of Samples 1008.04, 1022.05, 1048.01, and 1125.04

| | EAR ID NO. | POLLEN SOURCE[1] | % OLEIC | % OIL |
|---|---|---|---|---|
| 1 | 1001.001 × 1000 | 1125.04 | 63.3 | 8.4 |
| 2 | 1001.002 × 1000 | 1125.04 | 58.8 | 7.6 |
| 3 | 1001.003 × 1000 | 1125.04 | 61.5 | 7.5 |
| 4 | 1001.004 × 1000 | 1125.04 | 65.8 | 8.4 |
| 5 | 1001.005 × 1000 | 1125.04 | 62.0 | 6.8 |
| 6 | 1002.001 × 1000 | 1125.04 | 65.3 | 9.2 |
| 7 | 1002.002 × 1000 | 1125.04 | 60.8 | 7.2 |
| 8 | 1002.003 × 1000 | 1125.04 | 63.4 | 7.5 |
| 9 | 1002.004 × 1000 | 1125.04 | 59.8 | 7.3 |
| 10 | 1002.005 × 1000 | 1125.04 | 60.9 | 8.5 |
| 11 | 1003.001 × 1000 | 1125.04 | 64.8 | 8.7 |
| 12 | 1003.002 × 1000 | 1125.04 | 61.4 | 7.1 |
| 13 | 1003.003 × 1000 | 1125.04 | 57.8 | 7.7 |
| 14 | 1003.004 × 1000 | 1125.04 | 63.0 | 8.2 |
| 15 | 1003.005 × 1000 | 1125.04 | 64.6 | 8.1 |
| 16 | 1004.001 × 1000 | 1125.04 | 62.6 | 7.7 |
| 17 | 1004.002 × 1000 | 1125.04 | 51.5 | 7.6 |
| 18 | 1004.003 × 1000 | 1125.04 | 63.8 | 8.2 |
| 19 | 1004.004 × 1000 | 1125.04 | 63.4 | 8.2 |
| 20 | 1004.005 × 1000 | 1125.04 | 66.5 | 8.3 |
| 21 | 1005.001 × 1000 | 1125.04 | 61.4 | 7.9 |
| 22 | 1005.002 × 1000 | 1125.04 | 65.7 | 8.6 |
| 23 | 1005.003 × 1000 | 1125.04 | 65.6 | 10.1 |
| 24 | 1005.004 × 1000 | 1125.04 | 64.0 | 11.0 |
| 25 | 1005.005 × 1000 | 1125.04 | 65.1 | 9.2 |
| 26 | 1007.001 × 1000 | 1125.04 | 61.1 | 7.4 |
| 27 | 1007.003 × 1000 | 1125.04 | 61.3 | 7.8 |
| 28 | 1007.004 × 1000 | 1125.04 | 60.7 | 8.4 |
| 29 | 1007.005 × 1000 | 1125.04 | 53.4 | 7.4 |
| 30 | 1008.001 × 1000 | 1125.04 | 52.2 | 7.1 |
| 31 | 1008.002 × 1000 | 1125.04 | 54.7 | 8.6 |
| 32 | 1008.003 × 1000 | 1125.04 | 62.2 | 9.1 |
| 33 | 1008.004 × 1000 | 1125.04 | 51.3 | 8.4 |
| 34 | 1008.005 × 1000 | 1125.04 | 61.7 | 9.1 |
| 35 | 1009.001 × 1000 | 1125.04 | 62.3 | 7.6 |
| 36 | 1009.002 × 1000 | 1125.04 | 63.0 | 7.5 |
| 37 | 1009.003 × 1000 | 1125.04 | 65.3 | 7.0 |
| 38 | 1009.004 × 1000 | 1125.04 | 58.6 | 9.6 |
| 39 | 1009.005 × 1000 | 1125.04 | 61.6 | 8.1 |
| 40 | 1010.001 × 1000 | 1125.04 | 61.3 | 9.9 |
| 41 | 1010.002 × 1000 | 1125.04 | 64.3 | 8.5 |
| 42 | 1010.003 × 1000 | 1125.04 | 61.4 | 8.0 |
| 43 | 1010.004 × 1000 | 1125.04 | 62.5 | 8.3 |
| 44 | 1010.005 × 1000 | 1125.04 | 48.0 | 8.5 |
| 45 | 1011.001 × 1000 | 1125.04 | 47.0 | 10.2 |
| 46 | 1011.002 × 1000 | 1125.04 | 60.2 | 7.8 |
| 47 | 1011.003 × 1000 | 1125.04 | 59.4 | 7.7 |
| 48 | 1011.004 × 1000 | 1125.04 | 52.3 | 8.0 |
| 49 | 1011.005 × 1000 | 1125.04 | 60.3 | 8.3 |
| 50 | 1013.001 × 1012 | 1022.05 | 66.2 | 7.2 |
| 51 | 1013.002 × 1012 | 1022.05 | 64.0 | 9.2 |
| 52 | 1013.005 × 1006 | 1008.04 | 63.1 | 7.4 |
| 53 | 1013.006 × 1006 | 1008.04 | 60.3 | 7.6 |
| 54 | 1013.007 × 1006 | 1008.04 | 64.5 | 6.9 |
| 55 | 1014.003 × 1012 | 1022.05 | 62.4 | 7.6 |
| 56 | 1014.004 × 1012 | 1022.05 | 62.7 | 7.7 |
| 57 | 1014.005 × 1012 | 1022.05 | 61.4 | 8.0 |
| 58 | 1015.002 × 1012 | 1022.05 | 62.3 | 7.6 |
| 59 | 1015.003 × 1012 | 1022.05 | 63.7 | 6.8 |
| 60 | 1015.004 × 1012 | 1022.05 | 62.9 | 7.0 |
| 61 | 1016.002 × 1012 | 1022.05 | 54.5 | 7.5 |
| 62 | 1017.001 × 1000 | 1125.04 | 46.7 | 8.8 |
| 63 | 1017.002 × 1000 | 1125.04 | 60.6 | 8.9 |
| 64 | 1017.003 × 1000 | 1125.04 | 58.1 | 8.1 |
| 65 | 1017.004 × 1000 | 1125.04 | 60.0 | 7.8 |
| 66 | 1017.008 × 1018 | 1048.01 | 62.4 | 7.6 |
| 67 | 1019.001 × 1018 | 1048.01 | 64.4 | 6.1 |
| 68 | 1019.002 × 1018 | 1048.01 | 63.2 | 7.4 |
| 69 | 1019.003 × 1018 | 1048.01 | 62.7 | 6.8 |
| 71 | 1019.005 × 1018 | 1048.01 | 64.9 | 7.9 |
| 72 | 1020.002 × 1018 | 1048.01 | 63.2 | 7.9 |

TABLE 3-continued

Oil and Oleic Acid Content of Grain Resulting from the
Cross Pollination of B730L x AEC2720L Ears by Pollen
From F3 Derived Plants of Samples 1008.04,
1022.05, 1048.01, and 1125.04

| EAR ID NO. | | POLLEN SOURCE[1] | % OLEIC | % OIL |
|---|---|---|---|---|
| 73 | 1020.003 × 1018 | 1048.01 | 59.0 | 6.7 |
| 74 | 1020.004 × 1018 | 1048.01 | 61.5 | 6.4 |
| 75 | 1020.005 × 1018 | 1048.01 | 64.8 | 7.9 |
| 76 | 1020.006 × 1018 | 1048.01 | 65.1 | 7.1 |
| 77 | 1021.002 × 1018 | 1048.01 | 59.2 | 6.7 |
| 78 | 1021.003 × 1018 | 1048.01 | 66.8 | 7.5 |
| 79 | 1021.004 × 1018 | 1048.01 | 62.5 | 7.5 |
| 80 | 1021.006 × 1018 | 1048.01 | 63.6 | 8.0 |
| 81 | 1021.007 × 1018 | 1048.01 | 53.2 | 7.9 |
| 82 | 1022.001 × 1018 | 1048.01 | 64.5 | 7.7 |
| 83 | 1022.002 × 1018 | 1048.01 | 62.4 | 7.2 |
| 85 | 1022.004 × 1018 | 1048.01 | 62.8 | 6.5 |
| 86 | 1022.005 × 1018 | 1048.01 | 61.6 | 8.0 |
| 87 | 1023.002 × 1018 | 1048.01 | 62.8 | 7.6 |
| 88 | 1023.003 × 1018 | 1048.01 | 65.3 | 8.1 |
| 89 | 1023.004 × 1018 | 1048.01 | 62.8 | 7.1 |
| 90 | 1023.005 × 1018 | 1048.01 | 64.6 | 7.3 |
| 91 | 1023.007 × 1018 | 1048.01 | 62.2 | 8.3 |
| | AVERAGE | | 62.8 | 8.4 |

[1]Pollen source identifies the F3 plants derived from F3 ears described in Table 1.

In this example, the grain parent (B73OL X AEC272OL), when self pollinated, will produce grain with an oil content approximately two percentage points higher than normal corn (6% vs. 4%). The oil level obtained in grain described in Table 3 is due in part to the increased oil contributed by the grain parent. By using pollinator plants of the type described in this example, high oil, high oleic grain can also be produced on grain parents that, if self pollinated, would produce normal oil levels (i.e., 4%). To illustrate this point, plants of the background B73OL were pollinated by plants of the background LH60 (a product of the Holden's Foundation Seed Co., Williamsburg, Iowa) to produce F1 hybrid seed. LH60 is an inbred line having a normal (4%) oil level and higher than normal oleic acid level (35–40%). Self pollinated grain produced on B73OL X LH60 plants is 3–4% oil and 45–50% oleic acid. Yield tests have shown that the hybrid B73OL X LH60 is capable of matching or exceeding the grain yield of current elite hybrids. Grain having an oil content of 8.7% and an oleic acid content of 56.8% was produced by allowing B73OL X LH60 F1 plants to be pollinated by a bulk of F4 high oil, high oleic plants from the cross B73OL X ASKC28 described in Example 1. The bulk of F4 pollinator plants represented 165 F4 ears derived from 20 F3 ears that had an average oil content of 15.0% oil and 57% oleic acid. Grain parent and pollinator plants were planted in a repeating pattern of six grain parent rows to two pollinator rows. In maize, the male part of the plant is the tassel which can be easily removed by hand or machine.

Female grain parent plants were detassled by hand and the resulting grain arose from wind-born pollen from pollinator rows. Approximately 2000 pounds of grain was produced in this manner. However, to facilitate cross pollination on a commercial scale, the plants to be used as the female would be rendered male sterile. This can be accomplished by physical removal of the male pollen-shedding part of the plant, by chemical treatment, or by a genetic mechanism such as cytoplasmic male sterility. Grain yields comparable to those of fully male-fertile hybrid plants can be achieved by planting a mixture of seeds containing a small percentage of pollinator and a large percentage of male sterile grain parent, for example wherein the ratio of the pollinator to the male sterile female grain parent is approximately one to six.

This example illustrates the important point that the present invention offers a way to produce a high yield of grain with substantial increases in oleic acid content over normal corn. Also, this grain production method dramatically reduces the breeding timeline by allowing growers to utilize currently available high-yielding corn hybrids in combination with selected pollinators to produce grain with substantially higher oleic acid content.

Example 3

Use of High Oil, High Oleic Corn in an Animal Feed Ration as a Means of Improving Meat Quality By replacing some or all of the supplemental animal fat in a feed ration with the oil present in high oil, high oleic corn, it will be possible to produce meat products having less saturated fats. As discussed in the Background, the utility of this concept has been demonstrated in feeding trials with swine that were fed diets containing high oleic oil. In this example, a method of producing animals having less saturated fat and more monounsaturated fat by using a the present invention will be described. An important difference between this and the feeding trials described in the Background is that in this example, high oleic acid oil is supplied in the grain rather than as a supplement to the feed, offering greater convenience to animal producers. Feeding trials which have shown that adding oleic acid to the feed improves carcass quality typically use high oleic canola or sunflower oil. From a commercial standpoint, providing oleic acid in the grain rather than as a supplemental oil eliminates the cost, inconvenience, and time of handling an additional feed ingredient.

A protocol has been developed to evaluate the effects of feeding a high oil, high oleic corn type on several factors including:

A. the growth of swine,

B. the fatty acid composition of fat and muscle tissue,

C. the stability of carcass fat,

D. consumer preference of improved meat products.

Four feeding programs would be utilized to raise swine with improved carcass composition. Feeding Program 1 consists of a corn and soybean meal diet which contains no added fat. Feeding Program 2 consists of a high oil, high oleic corn plus soybean meal diet in which the relationships between critical nutrients on the caloric density are equal to those of Feeding Program 1. Feeding Program 3 consists of a corn and soybean meal diet with added crude corn oil formulated to achieve the same caloric density and nutrient to calorie relationships as Feeding Program 2. Feeding Program 4 consists of a corn and soybean meal diet with added animal fat formulated to achieve the same caloric density and nutrient to calorie relationships as Feeding Program 2.

To evaluate any interaction between hog genetic background and the above feeding programs, two hog types would be used in this study. Group 1 consists of hogs having a high productive performance and high lean gain potential with a mature body weight of over 240 pounds. Group 2 consists of hogs with a "classical" genetic potential for lean gain and productive performance with a mature body weight of under 220 pounds. The total number of experimental treatments for this phase of the experiment is 8, and includes 4 feeding programs and 2 hog types.

Diets need to be formulated for each treatment feeding program for each of four production stages. The production stages, based upon live body weight are as follows:

a. 45–90 pounds
b. 90–130 pounds
c. 130–200 pounds
d. 200–240 pounds

Four pens per treatment, and six pigs per pen, for a total of 192 pigs, are needed. At the beginning of the trial, pigs are to be weighed and allotted to pens, within a genetic potential treatment, in a manner which equalizes weight and sex across feeding program treatment. Pigs within each pen need to similar in weight and proportion of females versus barrows.

Hogs need to be weighed at the beginning of each production stage and at the end of the feeding period. The weight of feed added to the feeders in each pen must be recorded as it is added. Feed remaining in the feeder at the end of each production stage must be removed and weighed. Hogs are to housed in a confinement facility and feed and water are to be offered ad-libitum. Hogs within a genetic background treatment are to be sent to slaughter when they reach their mature body weight.

Hogs are to be slaughtered and processed in a commercial plant which purchases hags on the basis of grade and yield. Tissue samples from the ham and loin, and the subcutaneous fat surrounding these cuts must be obtained and saved for analysis. Samples of ham and loin from 1 pig from each pen is to be processed and saved for sensory evaluation.

Feeding performance can be evaluated by comparing the average daily gain, the average daily feed intake, and the feed efficiency (pounds of feed/pounds of gain) for each of the treatments. The effect of the treatments on carcass quality can be evaluated by measuring average carcass weight, average back fat, average percent lean yield, and average actual yield. The effect of the treatments on meat quality can be evaluated by analyzing the ham, loin, and the surrounding subcutaneous fat for fatty acid profile, oxidative stability, and meat firmness. Consumer related factors such as taste and appearance of ham and loin cuts must be evaluated by a trained and experienced sensory panel.

Example 4
Improved Functional Properties of Oil Extracted from High Oil, High Oleic Corn This example illustrates the improved oxidative stability and subsequent utility of oil extracted from high oil, high oleic corn. Crude oil was extracted from the grain samples described in Example 2, and from a bulk of normal corn hybrids. For each sample, approximately 4 pounds of clean grain was cracked using a Rosskamp model TRC-650-6 cracking roller. Oil extraction was done in a glass extraction vessel heated to 60° C. in a water jacket. Two gallons of hexane was added to the cracked grain in the extraction vessel, and the solvent cycled through the system for 45 minutes. After extraction, hexane was removed with a rotary evaporator, leaving crude oil. Corn oil used in commercial cooking applications or in food products is not used in its crude form, but rather is refined, bleached, and deodorized. The crude oil was processed using procedures designed to mimic those used by commercial manufactures of refined corn oil. Commercial conditions cannot be duplicated exactly on a laboratory scale. However, the conditions and procedures employed approximate those used commercially.

To refine, bleach, and deodorize the oil, 300 g of crude oil was placed in a 600 ml glass beaker and 0.3 g of $H_3PO_4$ was added dropwise while stirring as a 0.1% solution of 85% $H_3PO_4$. The sample was heated to 65–70° C. and held for 10 minutes. Warm (60° C.) NaOH (8%) was added dropwise to the oil sample to neutralize the free fatty acids and the $H_3PO_4$. The sample was stirred for 5 minutes, then split among centrifuge tubes and centrifuged for approximately 5 minutes at 2500 RPM. The soap film was swabbed from the top of the tube and oil was decanted into a clean beaker. The oil was then water washed with the addition of 20% (v/v) of hot water as the sample was heated to 90° C. with rapid agitation. The oil and water were allowed to stand and separate for 10 minutes and the sample was centrifuged again at 2500 RPM for 10 minutes. Oil was decanted into a small beaker to prevent the accidental contamination of the oil with the aqueous phase and then was poured into a 500 ml suction flask. The oil was dehydrated using very rapid agitation under vacuum at 85–95° C. for 30 minutes or until all moisture (bubbles, condensation) had been removed. The vacuum was then broken with nitrogen. Two percent (wt/wt) of Filtrol F-160 was added and the vacuum was again immediately applied slowly with rapid agitation for and additional 30 minutes at 85–95° C. While under vacuum, the oil was allowed to cool to 60° C. with reduced agitation. The vacuum was then broken with nitrogen and one percent (wt/wt) of diatomaceous earth was dispersed in the oil. The mixture was suction filtered through a prepared bed of diatomaceous earth supported by filter paper into a 500 ml suction flask.

Following refining and bleaching, the oil was deodorized in a deodorization vessel. The first trap of the vessel was filled with ice and water, the second trap was filled with liquid nitrogen. 4 ml of deionized water was added per 100 g of oil in the bioler portion of the vessel. Two drops of 25% citric acid were added to the vessel, then oil was added to the citric acid solution in the vessel. The sample was heated to 240° C. under vacuum and nitrogen flow at one PSI. Nitrogen flow was stopped when the sample reached 60° C. At completion of the deodorization process, the sample is cooled to 40° C. and the refined oil was removed to a flask.

Oleic acid percent of oil extracted from the samples was measured by gas chromatograph. The oleic acid level represents an average of four 20 g subsamples of grain.

Oil oxidation occurs in two stages, the first being the induction period, and the second being the exponential phase; Lin, S. S., Fats and Oils Oxidation, In: Introduction to Fats and Oils Technology, P. J. Wan, ed., American Oil Chemists Society, Champaign, Ill., pp. 211–231. Oxidation of an oil proceeds through free radical formation, hydroperoxide formation, and oxidation products formation. The first detectable products of oxidation are hydroperoxides. Once formed, the peroxides will begin to decompose and form volatile and non-volatile oxidation products. The volitile compounds generally have objectionable odors and can be smelled easily, the smell being one of rancidity or staleness. The non-volatile products can be further classified as polarized and polymerized compounds.

The length of time needed to produce a rapid acceleration of oxidation (the exponential phase) of oils and fats is indicative of resistance to oxidation. This length of time is measured as a mathematical determination of the maximum change of the rate of oxidation, and is known as the Oil Stability Index (OSI).

An OSI instrument, Omnion, Inc., Rockland, Mass., was used to predict the stability or resistance to oxidation by measuring the rate of volitile compound formation. Method Cd 12b-92 of the American Oil Chemists Society was used. Cleaning of the poly carbonate tubes and the conductivity probes accomplished with RBS 35 (FLUKA) and hot water.

5.0 g±0.2 g of oil sample was placed in disposable sample tubes. All connections were made according to the manufacturers directions and the samples were run at 110° C. Water supply is a Barnstead NANOpure II system with Type I, Organic Free and Pyrogen Free cartridges. Duplicates of each sample were performed in the same run. Placement of tubes in the OSI instrument was accomplished in a random fashion. Data were collected and OSI was determined on a DELL computer using software supplied by the manufacturer. Oils with high induction times as measured by the OSI are more resistant to oxidation than oils with low values (Table 4).

Heat accelerates oxidation of oils and alters the pattern of oxidation products. The temperature of an oil is generally kept between 180° and 250° C. during deep fat frying. At such temperatures, the oil will oxidize at a faster rate and the nature of oxidation will be different from the the nature of oxidation at room temperature. At frying temperatures, the formation of polymerized molecular species is generally greater. As a result, the oil will develop a dark color, have higher viscosity, and will foam easily. The polar and polymer indecies, as used here, reflect an oils ability to withstand heat and remain stable. A high index reflects rapid breakdown of the oil and rapid accumulation of polymeric and polarized breakdown products. The lower the index, the greater the ability of the oil to withstand the elevated temperatures used in frying applications.

The system for the analysis of the high temperature stability tests consists of a heating unit, a Rainin Instrument Dynamax HPLC and data acquisition system, two Rabbit-HP solvent delivery pumps, ICI Instrument's AS 2000 auto injector, and MiltonRoy spectromonitor UV detector at 254 nm. Five ml of oil per sample was placed in a 13×100 mm glass screw cap test tube. The tubes were placed in an aluminum heating block that holds 13 mm tubes. The aluminum block was heated by a Thermolyne type 1900 hot plate that is controlled with a PMC Dataplate 520 temperature controller with timer. This provides a consistent temperature of 180° C. in the aluminum block and provides auto off of the hot plate after ten hours. After 10, 20, 30, and 40 hours of heating time (10 hours per day over a 4 day period), a 50 microliter sample was removed and placed in a 2 ml screw cap HPLC vial with Teflon and silica septa for polar and polymer analysis.

Samples were placed in a −20° C. freezer until assayed. Just prior to HPLC analysis, samples were brought to room temperature. 950 microliters of hexane and 1.5% isopropyl alcohol were added and the samples were vortexed. Samples were placed in the autosampler of the HPLC for assay.

The HPLC column used is a Beckman Ultrasphere 4.6×25 cm. The method used is similar to that used by Lin; supra; who looked at the oxidation of soybean oil at elevated temperatures. The mobile phases were, Reservoir A: isopropanol, and Reservoir B: methanol. Starting conditions were 2 minutes at 40% A and 60% B, followed by a linear gradient change to 70% A and 30% B over a 7.5 minute time period. This was held for 4.5 minutes and then the gradient was changed linearly to 90% A and 10% B over 2.5 minutes. This was held for 2.5 minutes and then the gradient was changed linearly to 95% A and 5% B over 2.5 minutes and held for 22.5 minutes before returning to starting conditions over 5 minutes.

Resulting chromatographs were integrated and areas for polar and polymeric peaks in the samples were determined. The increase in polar and polymeric material over heating times was plotted and fitted with a regression equation. The resulting equation was integrated from 0 to 40 hours to determine the total area under the regression curves. The number representing the total area under the curve was given the name of polar index or polymer index. Table 5 shows polar and polymer indecies for normal corn oil and oil obtained from high oil, high oleic corn. Oils having lower polar or polymer indecies are more stable. The polarized and polymerized compounds that are generated during heating are the main causes of foaming and bitter taste during prolonged deep fat frying. Foods fried in oxidized oil become stale rapidly and have a short shelf life.

TABLE 4

Induction Time of Oil Obtained from Normal Corn and High Oil, High Oleic Corn Described in Examples 1 and 2

| Sample | % Oleic Acid | Induction Time (Hrs.) | Induction Time Standard Deviation |
|---|---|---|---|
| Normal Corn[1] | 30 | 6.1 | 0.07 |
| ASKC28OL[2] | 58 | 10.7 | 0.32 |
| (B73OL × AEC272OL) × ASKC28OL (Newark, DE, 1993) | 64 | 11.5 | 1.34 |
| (B73OL × AEC272OL) × ASKC28OL (Molokai, HI, 1993) | 63 | 13.2 | 0.28 |
| (B73OL × LH60) × ASKC28OL | 57 | 10.8 | 0.28 |
| LSD (0.05) | | 1.6 | |

[1]Normal corn consists of blended grain from four commercially grown hybrids.
[2]ASKC28OL represents a bulk of F4 high oil, high oleic plants from the cross B73OL × ASKC28 described in Example 1. The bulk of F4 pollinator plants represented 165 F4 ears derived from 20 F3 ears that had an average oil content of 15.0% oil and 57% oleic acid.

TABLE 5

Polar and polymer indecies of oil obtained from normal corn and high oil, high oleic corn described in Examples 1 and 2

| Sample | % Oleic Acid | Polar Index ± Std. Dev. | Polymer Index ± Std. Dev. |
|---|---|---|---|
| Normal Corn[1] | 30 | 187 ± 14 | 1078 ± 35 |
| ASKC28OL[2] | 58 | 142 ± 8 | 532 ± 71 |
| (B73OL × AEC272OL) × ASKC28OL (Newark, DE, 1993) | 64 | 121 ± 12 | 470 ± 25 |
| (B73OL × AEC272OL) × ASKC28OL (Molokai, HI, 1993) | 63 | 143 ± 21 | 528 ± 45 |
| (B73OL × LH60) × ASKC28OL | 57 | 182 ± 23 | 543 ± 33 |
| LSD (0.05) | | 43 | 115 |

[1]Normal corn consists of blended grain from four commercially grown hybrids
[2]ASKC28OL represents a bulk of F4 high oil, high oleic plants from the cross B73OL × ASKC28 described in Example 1. The bulk of F4 pollinator plants represented 165 F4 ears derived from 20 F3 ears that had an averagel oil content of 15.0% oil and 57% oleic acid Example 5
AEC272OL and B73OL can be Used to Produce Inbred Lines of Corn Expressing Elevated Levels of Oleic Acid Tables 6 and 7 demonstrate that B73OL and AEC272OL can be used effectively in a breeding program to increase the oleic acid content of many different corn inbreds. The data in Table 6 are taken from the most recently analyzed cycle of a partially completed backcross breeding program. Backcrossing is a conservative breeding method which is most often used to introduce simply inherited, highly heritable traits into existing agronomically elite inbred lines. In a typical backcrossing program involving a quality grain trait (i.e., a trait which influences the composition of a corn kernel, such as waxy), one or a series of varieties containing a quality grain trait are crossed to a series of elite inbred lines, which are termed recurrent parents. The progeny of these crosses are again crossed back to their respective recurrent parents, and this cycle is repeated typically 5 to 8 times. During this process the quality grain trait is maintained in each backcrossing project by visual or other selection, and the average nuclear genetic composition of each emerging inbred becomes closely similar to that of the elite recurrent parent. The result is the production of a series of elite inbred lines which express the newly introduced grain quality trait and in all other respects very closely resemble the plant type and combining characteristics of their respective recurrent parents. Finally, these finished inbreds are selfed and homozygous individuals selected so the quality grain trait is uniformly expressed in subsequent seed increases.

B73 as a line has given rise to a large number of elite female corn inbreds widely employed in commercial production today. Further, B73 is closely related to several of the inbreds employed as recurrent parents in Table A. This further increases the probability that elite inbreds will be recovered from backcrossing projects employing B73OL as a source of the high oleic trait. While not as elite as B73, AEC272 is a well adapted experimental high oil male inbred and performs reasonably well in prototype high oil hybrids, suggesting that inbreds derived from AEC272OL after backcrossing should again yield agronomically elite inbreds.

The data in Table 6 gives the range of oleic values observed in the selfed progeny of a number of backcross conversion projects in which AEC272OL or B73OL were used as donors of the high oleic oil trait. The level of oleic acid in these projects was determined by selfing partially backcrossed lines during each backcrossing cycle, bulking the resultant kernels (termed S1) individually by ear, and measuring the fatty acid composition of a representative sample of kernels by gas chromatography using a slight modification of the extraction and analytical methods described in Example 1. Due to the crossing protocol employed, and because oleic content in both AEC272OL and B73OL is most likely controlled by a single semidominant gene with additive effects, we expect the genes causing high oleic acid content to segregate in these populations and thus expect a broad range of oleic acid content across S1 ears in projects that continued to carry the high oleic traits. In contrast, if the high oleic acid trait was either not expressed in a particular genetic background or was lost by faulty selection during the backcrossing process, we would expect a typically narrow range of oleic content in the kernels from selfed ears, as is typical of inbred lines of corn. In this analytical run the range of oleic content seen upon analysis of several ears of each of the recurrent parent inbreds was typically about 5%.

TABLE 6

Percent Oleic Acid in Oil Extracted from Lines Undergoing Backcross Conversion Growth in 1994 in Molokai, Hawaii

| Recurrent Parent | Oleic Source | Backcross Generation (n) | % Oleic in BC(n) S1 | | |
|---|---|---|---|---|---|
| | | | Range | Average | Observations |
| LH59 | AEC272OL | 4 | 44–20 | 32.4 | 20 |
| LH60 | AEC272OL | 4 | 53–31 | 41.9 | 8 |
| LH61 | LH105 × B73OL | 4 | 33–27 | 30.4 | 4 |
| LH74 | LH105 × B73OL | 4 | 44–25 | 32.0 | 11 |
| LH82 | AEC272OL | 4 | 42–21 | 26.8 | 14 |
| LH85 | AEC272OL | 3 | 45–25 | 33.0 | 19 |
| LH132 | B73OL | 3 | 57–23 | 37.7 | 12 |
| LH132 | LH105 × B73OL | 4 | 40–23 | 28.3 | 18 |
| LH145 | LH105 × B73OL | 4 | 54–22 | 31.8 | 16 |
| LH146 | B73OL | 4 | 33–22 | 26.5 | 11 |
| LH150 | LH105 × B73OL | 3 | 26 | 26.4 | 1 |
| LH163 | AEC272OL | 4 | 43–29 | 34.0 | 12 |
| LH168 | LH82(4) × AEC272OL | 0 | 57–24 | 42.4 | 11 |
| LH169 | LH82(4) × AEC272OL | 0 | 53–24 | 35.9 | 13 |
| LH172 | LH82(5) × AEC272OL | 0 | 48–20 | 31.5 | 15 |
| LH172 | LH105 × B73OL | 3 | 39–23 | 33.1 | 6 |
| LH185 | LHS9(5) × AEC272OL | 0 | 43–22 | 31.1 | 8 |
| LH186 | LH59(5) × AEC272OL | 0 | 33–20 | 25.7 | 10 |
| LH192 | LH105 × B73OL | 4 | 58–37 | 43.8 | 16 |
| LH192 | AEC272 | 4 | 61–37 | 46.2 | 14 |
| LH195 | LH105 × B73OL | 3 | 55–27 | 32.3 | 18 |
| LH197 | LH105 × B73OL | 4 | 62–27 | 39.0 | 19 |
| LH198 | LH105 × B73OL | 3 | 50–37 | 44.0 | 4 |
| LH199 | 132(5) × B73OL | 0 | 40–29 | 34.4 | 2 |
| LH200 | LH105 × B73OL | 4 | 43–26 | 34.6 | 5 |
| LH206 | LH150(5) × LH150 × B73OL | 0 | 43–24 | 31.4 | 10 |
| LH206 | LH105 × B73OL | 4 | 47–30 | 38.1 | 9 |
| LH211 | LH105 × B73OL | 4 | 35–21 | 26.1 | 8 |
| LH212 | LH216(5) × AEC272OL | 0 | 31–20 | 25.1 | 10 |
| LH213 | LH216(5) × AEC272 | 0 | 45–25 | 34.4 | 13 |
| LH213 | LH18 × B73OL | 3 | 58–33 | 46.1 | 8 |
| LH216 | AEC272OL | 4 | 36–24 | 30.5 | 6 |

TABLE 6-continued

Percent Oleic Acid in Oil Extracted from Lines Undergoing Backcross Conversion Growth in 1994 in Molokai, Hawaii

| Recurrent Parent | Oleic Source | Backcross Generation (n) | % Oleic in BC(n) S1 | | |
|---|---|---|---|---|---|
| | | | Range | Average | Observations |
| LH218 | LH216(5) × AEC272OL | 0 | 31–18 | 24.3 | 11 |
| LH219 | LH216(5) × AEC272OL | 0 | 34–25 | 28.8 | 9 |
| LH223 | B73OL | 4 | 45–28 | 34.2 | 10 |
| LH225 | LH18 × B73OL | 4 | 51–26 | 34.3 | 15 |

Out of the 36 backcross projects presented in Table 6 17 exhibited a range of oleic acid contents of 20 percentage points or greater, while 16 exhibited a range of oleic acid content of 11 percentage points or greater. Of the remaining projects LH150 returned only one ear during this cycle and hence failed to show a range of segregation, and the oleic trait may have been lost during the course of the LH61 and LH219 backcross projects. Overall, these results indicate that B73OL and AEC272OL can be used as effective donors of the high oleic acid trait, and that the high oleic trait is expressed at sufficiently high levels in a number of genetic backgrounds to allow simple, effective selection during backcross breeding.

Oil extracted from B73OL and AEC272OL kernels typically exhibits oleic acid levels of 60%. These levels of oleic acid are generally not seen in Table 6 because none of the S1 ears examined are expected to be homozygous for the oleic genes present in either AEC272OL or B73OL. To gain an estimate of the final oleic acid level which may be achieved in finished lines after backcross conversion, plants from the second backcross generation (BC2) from several backcross projects were self pollinated to yield a BC2S1 kernels. Ears bearing BC2S1 kernels exhibiting elevated oleic contents when bulked were replanted in a field in Newark, Del. in the summer of 1994 and resultant plants were self pollinated to yield BC2S2 kernels. It was expected that a proportion of these BC1S2 plants would be homozygous for the high oleic gene present in B73OL and AEC272OL and that kernels obtained from BC2S2 ears from these homozygous plants would be uniformly high in oleic acid content. Kernels produced on the remainder of the BC2S2 ears would either exhibit oleic acid levels typical of corn inbreds or would contain a mixture of grain types. The upper range of oleic acid content seen in BC2S2 ears should thus be indicative of the expression of kernels uniformly expressing the high oleic trait. Since approximately 87% of the nuclear genome of BC2S2 kernels should be derived from the recurrent parent, these oleic levels should be generally representative of the oleic acid content of oil extracted from seeds of the finished inbreds when these backcrossing projects are completed.

TABLE 7

Percent Oleic Acid in Oil Extracted from Bulked BC252 Kernels Produced in Newark, Delaware During Summer 1994

| Recurrent Parent | Oleic Source | Percent Oleic, BC2S2 | | |
|---|---|---|---|---|
| | | Range | Average | Observations |
| LH59 | AEC272OL | 64–24 | 40.4 | 49 |
| LR60 | AEC272OL | 59–43 | 43.6 | 39 |
| LR61 | LR105/B73OL | 62–24 | 39.6 | 44 |

TABLE 7-continued

Percent Oleic Acid in Oil Extracted from Bulked BC252 Kernels Produced in Newark, Delaware During Summer 1994

| Recurrent Parent | Oleic Source | Percent Oleic, BC2S2 | | |
|---|---|---|---|---|
| | | Range | Average | Observations |
| LH74 | LR105/B73OL | 62–26 | 40 | 16 |
| LH82 | AEC272OL | 58–23 | 38.1 | 55 |
| LH85 | AEC272OL | 61–23 | 36.7 | 51 |
| LR132 | LH105/B73OL | 63–23 | 40.22 | 51 |
| LH132 | B73OL | 58–22 | 39 | 50 |
| LR145 | LH105/B73OL | 67–22 | 37.3 | 43 |
| LH146 | B73OL | 64–22 | 40.8 | 48 |
| LH150 | LH105/B73OL | 53–27 | 39.1 | 15 |
| LR163 | AEC272OL | 58–26 | 39.5 | 45 |
| LR172 | LH105/B73OL | 60–24 | 36.4 | 34 |
| LR192 | LH105/B73OL | 70–32 | 52 | 46 |
| LR192 | AEC272OL | 70–25 | 53.2 | 31 |
| LR195 | LH105/B73OL | 61–22 | 35.6 | 55 |
| LR197 | LH105/B73OL | 60–24 | 40.7 | 56 |
| LR198 | LH105/B73OL | 68–26 | 42.6 | 53 |
| LH200 | LH105/B73OL | 62–25 | 39.9 | 56 |
| LR206 | LH105/B73OL | 50–24 | 35.6 | 44 |
| LH211 | LR105/B73OL | 55–24 | 33.8 | 31 |
| LH212 | LR105/B73OL | 62–22 | 41.8 | 34 |
| LH213 | LR18 × B73OL | 56–28 | 39.6 | 25 |
| LH216 | AEC272OL | 47–25 | 32.2 | 33 |
| LH223 | B73OL | 48–26 | 36.2 | 28 |
| LH225 | LR18 × B73OL | 48–30 | 41.3 | 20 |

Out of the 26 backcross projects examined in Table 6 19 returned ears with kernels containing oil with an oleic acid content of 57% or greater. Four of these projects contained oil with an oleic acid content of 65% or greater, and the two backcross projects involving LH192 as recurrent parent returned ears whose kernel oil contained 70% oleic acid. Table 7 further illustrates that it is possible to recover high oleic segregants in the LH61 project and hence the failure to recover high oleic LH61 segregants in Table 6 is more likely due to missed selection during the latter stages of the backcrossing program rather than by any suppressive effect of the LH61 background.

Overall, it appears that both AEC272OL and B73OL will be effective in producing inbred lines of corn by the backcross method of breeding which in most cases will produce kernels whose oil will contain approximately 60% oleic acid. In some genetic backgrounds the final percentage of oleic acid is likely to approach 70%. It is further likely that breeding methods other than those employed during backcross conversion will also be effective in producing new inbreds containing oil which in many cases contains approximately 60% oleic acid, because the inheritance of the oleic trait from these sources is simple, the trait is highly selectable, and does not exhibit a high enough degree of either genotypic or environmental variability to adversely effect selection. Since the oil of selfed kernels from the hybrid B73OL X AEC272OL is itself 60% oleic acid, it is very likely that inbreds derived from either B73OL or AEC272OL can by combined in hybrid combination to produce hybrid corn grain containing oil with approximately 60% oleic acid content.

Example 2 teaches the production of grain containing oil with an oleic acid content of approximately 60% when utilizing various combinations of AEC272OL, B73OL, ASKC28OL, and standard corn inbreds. The data presented in Example 5 suggest that similar combinations made between suitably selected inbreds derived from either AEC272OL or B73OL and the high oil, high oleic pollinator ASKC28OL or derivatives will similarly produced grain containing approximately 6.5 to 10% oil, which oil has a content of approximately 60% oleic acid.

What is claimed is:

1. A corn grain produced by planting in close proximity a corn plant of an agronomically elite high-yielding female parent, having high oleic characteristics, and optionally having high-oil characteristics, with a corn plant of a high-oil and high oleic male parent, optionally having high-yielding characteristics and/or agronomically elite characteristics wherein said corn grain has an oil content of at least 6.5% on a dry weight basis and further wherein said oil is comprised of not less than about 55% oleic acid and the total oleic acid content of the grain is about 3.6% to about 7% of the total seed weight.

2. The grain of claim 1 wherein the high-oil, high oleic male parent plant, when self or sib pollinated, is capable of producing kernels having a total oil content ranging from 7.5% to 20% of the total seed weight, measured at zero percent moisture and an oleic acid content of not less than about 55% of the total oil content of the seed.

3. The grain of claim 1 wherein the agronomically elite female parent, when self or sib pollinated, is capable of producing kernels having a total oil content of between about 2 percent to about 7.5 percent of the total seed weight, measured at zero percent moisture, wherein the oleic acid content is not less than about 55% of the total oil content.

4. The corn grain of claim 1 wherein the high-oil, high oleic male parent, when self or sib pollinated, is capable of producing kernels having a total oil content ranging from 7.5% to 20% of the total seed weight, measured at zero percent moisture and an oleic acid content of not less than about 55% of the total oil content of the seed and wherein the agronomically elite female parent, when self or sib pollinated, is capable of producing kernels having a total oil content of between about 2 percent to about 7.5 percent of the total seed weight, measured at zero percent moisture, wherein the oleic acid content is not less than about 55% of the total oil content.

5. The grain of claim 4 wherein the female parent has an oil content of of not less than 6% of the total seed weight, measured at zero percent moisture.

6. The grain of claim 4 wherein the oleic acid content is about 3% to about 7% of the total seed weight.

7. Progeny plants and plant parts from any pedigree derived from the corn grain of claim 1.

8. Progeny plants and plant parts from any pedigree derived from the corn grain of claim 2.

9. Progeny plants and plant parts from any pedigree derived from the corn grain of claim 4.

10. Corn plants and the seed thereof regenerated from a tissue culture of the plant or plant parts selected from the group consisting of claims 7, 8, and 9.

11. The grain of claim 1, claim 3 or claim 4 wherein the female parent that is crossed to produce such grain is rendered male sterile by chemical, mechanical, or genetic means.

12. The corn grain of claim 4 wherein the high oleic characteristics of both the female plant and the male plant are generated from a high oleic corn inbred line designated B73OL which bears the ATCC accession number 97026.

13. The corn grain of claim 4 wherein the high oleic characteristics of both the female plant and the male plant are generated from a high oleic corn inbred line designated AEC272OL which bears the ATCC accession number 97027.

14. The corn grain of claim 4 wherein the high oleic characteristics of the female plant are generated from a high oleic corn inbred line designated B73OL which bears the ATCC accession number 97026 and the high oleic characteristics of the male plant are generated from a high oleic corn inbred line designated AEC272OL which bears the ATCC accession number 97027.

15. The corn grain of claim 4 wherein the high oleic characteristics of the female plant are generated from a high oleic corn inbred line designated AEC272OL which bears the ATCC accession number 97027 and the high oleic characteristics of the male plant are generated from a high oleic corn inbred line designated B73OL which bears the ATCC accession number 97026.

16. The corn grain of claim 1, wherein the corn grain borne by the female parent plant only, produced from the planting in close proximity, is selectively harvested, where such corn grain is substantially free of grain produced by self pollination of the female.

\* \* \* \* \*